US005848122A

United States Patent [19]
Kurtz

[11] Patent Number: 5,848,122
[45] Date of Patent: Dec. 8, 1998

[54] APPARATUS FOR RAPID IN-SITU X-RAY STRESS MEASUREMENT DURING THERMAL CYCLING OF SEMICONDUCTOR WAFERS

[75] Inventor: David S. Kurtz, State College, Pa.

[73] Assignee: Advanced Technology Materials, Inc., Danbury, Conn.

[21] Appl. No.: 823,967

[22] Filed: Mar. 25, 1997

[51] Int. Cl.⁶ ................................................. G01N 23/20
[52] U.S. Cl. ............................... 378/80; 378/79; 378/87
[58] Field of Search .................................. 378/70, 71, 72, 378/79, 86, 87

[56] References Cited

U.S. PATENT DOCUMENTS

| | | | |
|---|---|---|---|
| 3,727,052 | 4/1973 | Hino | 378/80 |
| 3,934,138 | 1/1976 | Bens | 378/72 |
| 4,078,175 | 3/1978 | Fletcher et al. | 378/72 X |
| 4,489,425 | 12/1984 | Borgonovi . | |
| 4,686,631 | 8/1987 | Ruud . | |
| 4,821,302 | 4/1989 | Whitlock et al. | 378/72 X |
| 4,821,303 | 4/1989 | Fawcett et al. | 378/80 |
| 5,125,016 | 6/1992 | Korhonen et al. . | |
| 5,148,458 | 9/1992 | Ruud . | |
| 5,414,747 | 5/1995 | Ruud et al. . | |

OTHER PUBLICATIONS

Noyan, I.C. and Cohen, J.B., "Residual Stress," Springer–Verlag, ISBN 0–387–96378–2, (1987), pp. 4–7, 74–110, and 116–125. no month.

Noyan, I.C. and Goldsmith, C.C., "Thermal Stress Relaxation in Vapor Deposited Thin Films," Advances in X–ray Analysis, 34, 587, (1991). no month.

Crowder, C.E. et al., "The Measurement of Triaxial Residual Stress in Polymer–Coated Aluminum Circuitry in Microchip Modules," Advances In X–ray Analysis, 36, 231, (1993). no month.

Tencor FLX, "Thin Film Stress Measurement Systems," (1994). no month.

*Primary Examiner*—David P. Porta
*Attorney, Agent, or Firm*—Steven J. Hultquist; Oliver A.M. Zitzmann

[57] ABSTRACT

An apparatus for making rapid in-situ thermal stress measurements includes a controlled atmosphere test chamber for receiving and holding a test sample, and a heating zone within the test chamber confined to the near vicinity of the test sample. A test sample holder, a test sample heater, an x-y translation stage and a rotating stage are mounted within the test chamber. An X-ray source is positioned for producing an incident X-ray beam directed at the test sample from different inclination angles. The incident X-ray beam passes through a long but narrow X-ray window in the test chamber, diffracts from the test sample back through the same X-ray window and continues outside of the chamber to an X-ray detector. The diffracted X-ray beam is converted to light. The light is transmitted through optical fibers and is detected by a CCD array. The invention uses an advantageous scintillation material and a slow scan, fiber-optic compatible CCD photo-sensor array. This photo-sensor array enables the use of a long active detector along the 2θ arc and a long working distance between the test sample and the detector.

16 Claims, 5 Drawing Sheets

APPARATUS FOR RAPID IN-SITU X-RAY STRESS MEASUREMENT DURING THERMAL CYCLING OF SEMICONDUCTOR WAFERS

FIELD OF THE INVENTION

Invention relates to test apparatus and more specifically to X-ray diffraction apparatus for determining strain or stress in materials.

BACKGROUND OF THE INVENTION

During semiconductor processing, determination of stress during thermal treatment is very critical. For example, aluminum interconnects have a much higher thermal expansion coefficient than the substrate silicon wafer. During heating, compressive stresses develop in the aluminum coating, and upon cooling the stress becomes tensile. The aluminum interconnects are subjected to numerous thermal cycles as a part of the sequence of processing steps. The stresses developed during such processing steps can lead to premature failure of the interconnect. The stresses in part depend on the rate of heating and/or cooling, on the geometry of the aluminum coating and of neighboring barrier and passivation layers, and on the alloy content.

There are two general non-contact techniques for measuring stress in thin films used in semiconductor processing. In each of these methods the strain is directly measured, and a stress value is subsequently calculated.

The first technique, or laser reflection method for measuring stress in film coatings, commonly utilizes a laser beam that is reflected off the sample surface. This technique measures the amount of bowing created in the wafer by the subject film coating. The reflection angle of the laser beam changes as a function of the curvature of the wafer. Stress in the film coating is computed as follows:

$$\text{Film stress}=[E/(1-n)][h^2/6Rt], \text{ wherein} \quad (1)$$

E/(1−n)=substrate biaxial elastic modulus
h=substrate thickness
R=substrate radius of curvature
t=film thickness The laser reflection method is essentially a macroscopic technique that measures how curved the entire substrate is before and after a specific single thin film is applied. The laser reflection method is both simple and rapid to perform. It is fast enough to measure the change in stress during a thermal cycling process. After initially determining a baseline uncoated wafer curvature, a planar stress value from a single radial curvature scan can be completed in 15 to 30 seconds. In addition to determining stress, the magnitude of curvature itself is a very useful parameter in optimizing the manufacturing process. The laser reflection method is used to measure stress of single uniform blanket films that are crystalline or amorphous as long as those films produce a sufficient change in curvature of the substrate wafer. Two examples of commercial laser reflection thin film stress measurement systems are the Tencor Model FLX-2320 from Tencor Instruments and the FSM Model 500TC from Frontier Semiconductor Measurements Inc.

There are several disadvantages to the laser reflection technique. With respect to Equation (1) the substrate thickness h and the film thickness t must be uniform and precisely known for determining the planar stress with reasonable accuracy. The baseline curvature of the same wafer prior to deposition of the single thin film must be precisely determined on the laser reflection system for effective stress analysis. Substrate wafers such as silicon often exhibit some level of warpage due to residual stress in the wafer itself. If the substrate curvature is not precisely determined prior to coating with a thin film or if the curvature is determined on another substrate wafer from the same batch, unacceptable data scatter occurs. In practice, the laser reflection method is only accurate for a single, uniform, continuous coating applied to the substrate wafer, for which the wafer curvature is measured before the coating is applied and after the coating is applied. If the substrate wafer is much thicker than a typical silicon wafer used in semiconductor processing, then sufficient change in the curvature is not observable. If there are multiple coatings applied or if the coating is not continuous, but rather divided into discreet structures, the laser reflection method is ineffective. The laser reflection method does not measure stress gradients through the thickness of the coating nor stress in different layers at the same time. It determines only the direct planar stress, or average directional stress within the plane of the coating, with a radial direction of the stress corresponding to a radial direction of a curvature scan.

A second technique for non-contact stress measurement in thin films makes use of X-ray diffraction (XRD). X-ray diffraction has long been a powerful analysis tool for measuring residual stress, specifically with the use of a four circle (four axis rotation) scanning diffractometer. During X-ray diffraction testing, the position of the diffraction peak caused by the crystallographic structure of the film shifts in response to crystallographic strain, i.e., a change in the lattice 'd' spacing. Thus the X-ray diffraction method measures strain on the atomic scale, independent of the substrate thickness, film thickness, or overall curvature. X-ray diffraction relies on a periodic crystal structure. Only those coatings which exhibit crystallinity can be directly measured using the X-ray diffraction method. In the field of semiconductor processing, metal interconnect layers, and other discrete structures are sufficiently crystalline to be suitable for diffraction analysis. The lattice 'd' spacing can be determined from Bragg's Law:

$$n\lambda = 2d \sin\theta, \text{ wherein} \quad (2)$$

n=integer
$\lambda$=X-ray beam wavelength
d=lattice spacing
$\theta$=angle between incident X-ray beam and sample surface As a material becomes strained, the value of 'd' changes from an unstressed value to a stressed value. The change of 'd' causes the diffraction peak to shift from one angle $\theta_1$ to a different angle $\theta_2$. Thus the shift of the diffraction peak is directly related to the strain. For isotropic materials strains can be converted to stress using the following equation:

$$\text{stress } (\sigma)=[(d_\psi-d_o)/d_o][E/(1+v)][1/\sin^2\Psi], \text{ wherein} \quad (3)$$

$\Psi$=angle subtended between a line normal to the test surface and a line bisecting incident and diffracted X-ray beam
$d_\psi$=lattice spacing of the stressed state
$d_o$=lattice spacing of the unstressed state
$(d_\psi-d_o)/d_o$=strain of the stressed state
E/(1+v)=X-ray elastic constant By determining the change in 'd' spacing at different $\Psi$ angles, one can determine a directional planar stress from the slope of a plot of 'd' versus $\sin^2\Psi$. This method for determining directional planar stress is referred to as the $\sin^2\Psi$ technique or the multiple exposure technique (MET). See "Residual Stress," by I. C. Noyan and J. B. Cohen, Springer-Verlag, ISBN0-387-96378-2, 1987.

There are disadvantages to the X-ray diffraction method of determining stress. Commercial four circle scanning diffractometers are very slow in determining stress because they use a sequential scanning point detector and because there is only a limited amount of material available for diffraction in a thin film coating. For example, a single diffraction peak of a continuous 0.75 micron thick aluminum thin film coating typically requires at least six minutes of peak collection time on a 3 kW sealed beam scanning diffractometer. For the determination of stress in one planar direction using the common $\sin^2\Psi$ technique, multiple diffraction peaks are needed for obtaining a reproducible stress value. If for instance eight peaks are used, a total data acquisition time of forty-eight minutes is required for a single stress value. Even when high power rotating anode X-ray sources are used in conjunction with very limited peak scans on uniform blanket coatings, fifteen to twenty minutes are required to determine stress. See for example, "Thermal Stress Relaxation in Vapor Deposited Thin Films" by I. C. Noyan and C. C. Goldsmith, Advances in X-ray Analysis, 34,587, (1991). These times are too long for measuring stress during a typical thermal cycling process.

In spite of the slow data acquisition times and the limitation to crystalline coatings, the X-ray diffraction method has many advantages over laser reflection. Since it observes the strain directly in the irradiated volume of the material in question, it is completely independent of substrate thickness and film thickness. It is independent of the substrate curvature prior to the coating being applied. It does not matter whether the coating is a single continuous film or not. The region of interest can be a series of interconnect lines or bond pads, or a discreet structures that are overcoated with barrier and/or passivation layers because the X-rays readily penetrate such layers used in semiconductor processing. See for example, "The Measurement of Triaxial Residual Stress in Polymer-Coated Aluminum Circuitry in Microchip Modules", by C. E. Crowder, M. J. Radler and P. Townsend, Advances in X-ray Analysis, 36, 231, (1993).

A third technique can rapidly and easily determine residual stress using a fiber-optic based X-ray diffraction system, as described in U.S. Pat. Nos. 4,686,631, 5,125,016, 5,148,458, and 5,414,747. Although this fiber-optic X-ray technique is faster than the four circle scanning diffractometer, it is still slower than the laser reflection system. Since the fiber-optic based X-ray stress analyzer uses two position sensitive detectors, it can perform a more rapid single exposure technique that only measures the diffraction peaks at just two $\Psi$ angles. The fiber-optic X-ray technique requires forty to one hundred twenty seconds to determine a stress value using the abbreviated single exposure technique. When used for stress measurement during high temperature thermal cycling of a typical silicon wafer, it is adversely affected by a short working distance between the measuring head and the heated wafer surface. The short working distance results in unavoidable heating of the measuring head. Significantly increasing the working distance of the measuring head is not possible because the required angular $2\theta$ range would be lost. An insulating layer would not fit between the X-ray source and heated wafer, nor would it allow the X-rays to reach the wafer. Thus the present fiber-optic X-ray diffraction stress analyzer is not capable of rapid determination of stress in semiconductor structures subject to short heating cycles.

SUMMARY OF THE INVENTION

This problem is resolved by an apparatus for making rapid in-situ thermal stress measurements. The apparatus includes a thermal chamber for receiving and holding a test sample. A test sample holder and heater are moveably mounted within the chamber. An X-ray source is positioned to emit an X-ray beam directed at the test sample. The X-ray beam diffracts from the test sample to an X-ray window in the chamber for passing the X-ray beam outside of the chamber to detection and signal processing equipment.

The invention uses an advantageous scintillation material and a slow scan, fiber-optic compatible CCD photo-sensor array. This CCD photo-sensor array has a long length of active detector along the $2\theta$ arc, is used at a long working distance between the test sample and the detector, and is very fast.

Advantageously the apparatus can perform very rapid thermal stress measurements on semi-conductor wafers.

BRIEF DESCRIPTION OF THE DRAWINGS

A better understanding of the arrangement and operation of the described apparatus for performing X-ray stress measurements can be derived from reading the following detailed description with reference to the drawings wherein.

DETAILED DESCRIPTION

Figure 1:
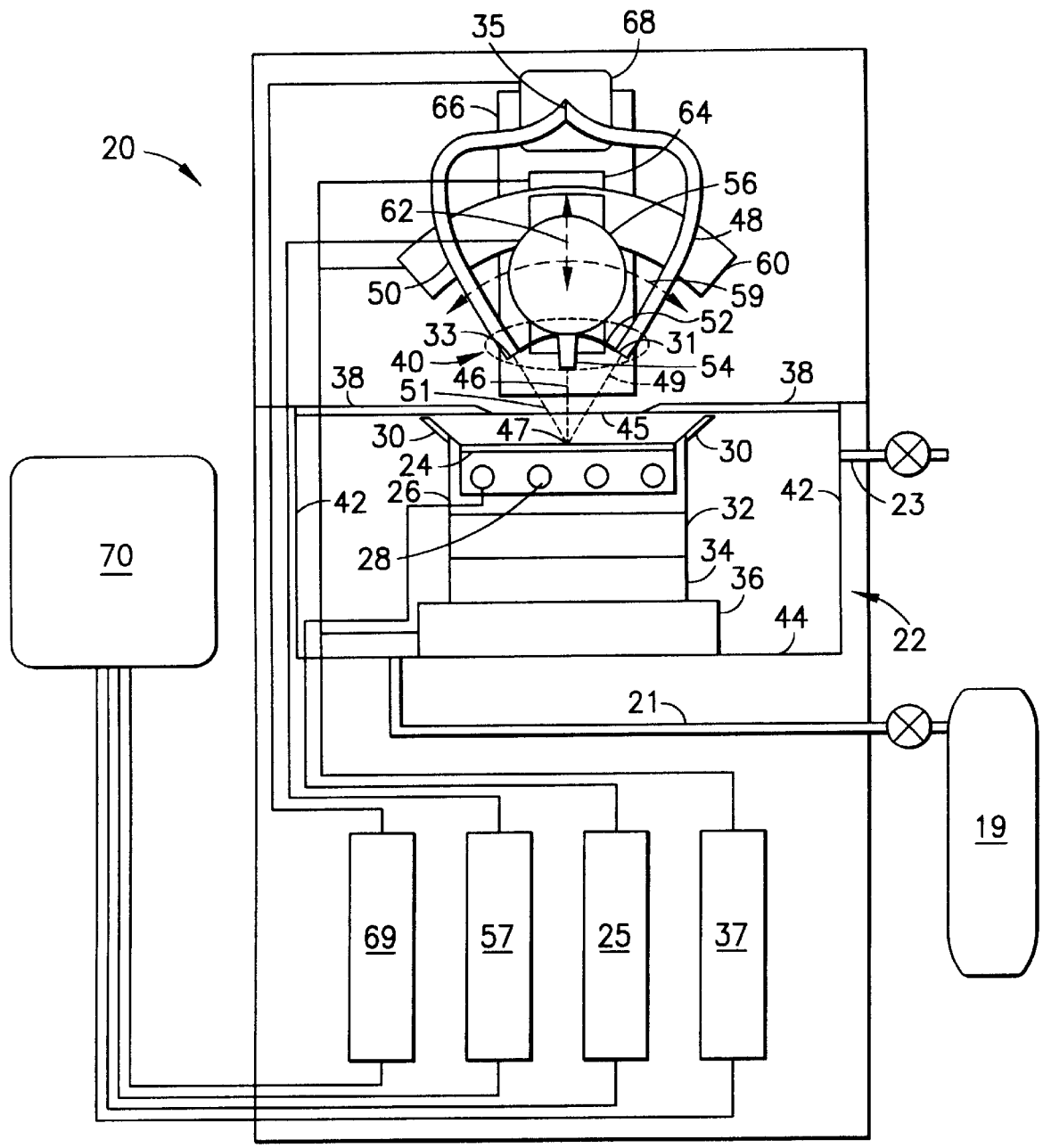
FIG. 1 is a schematic diagram of an X-ray stress measurement apparatus.

Referring now to FIG. 1, there is shown a test apparatus 20 for performing X-ray stress measurements on a test sample during thermal cycling. A controlled atmosphere test chamber 22 is designed for either operating at atmospheric pressure or at a vacuum. When operated at atmospheric pressure, a purge gas, e.g., nitrogen, source 19 can be used to direct a desired gas to the test chamber via line 21. That gas is vented to an appropriate exhaust location via line 23. A test sample 24, such as a semiconductor wafer, sits in a low profile test sample heater 26 which is well insulated on the bottom and sides. Removal of the wafer 24 from the test chamber 22 can be accomplished by making a top thermal barrier plate 38 removable, or by making a portion of it removable. Although not shown, an automated method of placing and removing wafers can be combined with an automated lid removal mechanism if so desired. The apparatus is arranged for complete wafer mapping, complete directional stress measurement, and complete thermal cycling, all implemented concurrently.

Most of the heat from the heater 26 is directed upward to the test sample 24 by resistive heating elements 28. Other heating elements such as quartz lamps would also be acceptable. The heater 26 has a low thermal mass to enable rapid heating, and is well insulated on the sides and bottom to avoid undesirable heat loss to other parts of the test chamber 22. Since the test sample will often be a large (two hundred millimeter diameter) thin silicon wafer, it will be critical to maintain a uniform temperature across the wafer during heating and cooling. A thermal chuck, normally used for wafer probing stations, can be used for the test sample heater 26. The heating and cooling profiles are controlled by a programmable temperature controller 25, such as the Model CN3000 from the Omega Co. A temperature, i.e., heating and cooling, profile is a time dependent temperature function. The rate of change of temperature is of particular concern. To have more positive control over the cooling rate, air or water is circulated through cooling lines within the heater 26 and is regulated by a flow control valve in response to a temperature controller. The perimeter of the test sample heater 26 can optionally incorporate a skirt 30 that extends from the test sample heater 26 to just below the bottom surface of the top thermal barrier plate 38. The skirt 30 does not touch the top thermal barrier plate 38 in order to avoid any friction which might interfere with desired movements of the test sample 24. The skirt 30 simply confines heat to a zone within the skirt to help prevent unwanted transfer of heat to other parts of the test chamber 22. The region bounded by the test sample 24, the perimeter skirt 30, the top thermal barrier plate 38, and an X-ray window 45, defines a controlled heating and cooling zone in which most of the heat is confined around the test sample and a small space above the sample.

The major direction of heat loss from the heated test sample 24 is upward toward the top thermal barrier plate 38. Some limited heat loss will occur through the X-ray window 45 separating a measuring head 40 from the top surface of the test sample 24, however, the X-ray window 45 is kept very narrow to minimize heat loss. Walls 42 and a bottom face 44 of the test chamber 22 will remain close to room temperature and can be constructed from traditional engineering materials such as metal alloys. A range of temperatures from 0° C. to 500° C. for the test sample 24 is appropriate for semiconductor thermal stress analysis. The top thermal barrier plate 38 is designed as an effective thermal barrier with good insulating properties. It can be fabricated from a low density, hard surface ceramic material that has both sufficient structural integrity and high thermal resistance. In the air space between the top thermal barrier plate 38 and the measuring head 40, some limited temperature rise might occur at high wafer temperatures, however, the rise can be limited by circulating fresh air through this air space and around the measuring head 40.

The measuring head 40 is situated above the heated test sample 24 which is contained within the test chamber 22. The measuring head includes a sealed tube, high voltage X-ray source and housing 56, a shutter assembly 54, a detector mounting arc 52, and two fiber-optic detectors 48 and 50. The X-ray source is operated by a standard high voltage controller 57. A collimator which controls the size and shape of the emanating X-ray beam 46 also resides in the shutter assembly 54. The measuring head 40 is attached to the X-ray tube housing 56, which is attached to a curved linear motion stage 60, that is referred to as a beta (β) goniometer. The measuring head 40 can rotate along the beta (β) beta arc 59, such that the emanating X-ray beam 46 can make an angle as large as 45° with the vertical direction. The angle between the emanating X-ray beam 46 and the direction normal to the test sample is referred to as the β angle. The distance from the shutter assembly 54 to the measurement position 47 is adjusted to exactly match the center of concentricity of a curved arc traversed by the measuring head 40. This means that the measurement position 47 is always at the center of rotation of the detector mounting arc 52. Thus, regardless of the β angle of the emanating X-ray beam 46, the X-ray beam 46 will always impinge upon the surface of the test sample at the same measurement position 47. The reference radial distance that is used to define the center of concentricity is the distance from the measurement position 47 to the detector mounting arc 52, which also defines the exact location of the receiving end surfaces of detectors 33 and 31. This is referred to as the working distance and is equal to the length of the diffracted X-ray paths 49 and 51. By utilizing other detector mounting arcs having a different radii and mounting the X-ray source 56 at different offset elevations from the beta goniometer 60, an operator can control the working distance.

The combination of the measuring head 40, the X-ray source and housing 56, and the beta goniometer 60 is attached to a vertical motion stage 64 that enables limited motion of the measuring head 40 in the vertical (z) 62 direction. This allows one to maintain the same required working distance regardless of minor changes in the test sample thickness. The vertical motion stage 64 and the beta goniometer 60 are both operated by controller 37, which also operates positioning stages 32, 34, and 36, located within the test chamber and to be described.

Regardless of the beta or z-axis position, the X-ray beam 46 is always directed to the measurement position 47 within the test chamber 22. This measurement position will be essentially at the center of the test chamber footprint at an elevation equivalent to the top surface of test sample 24. Located within the test chamber 22 beneath the test sample heater 26 is a linear 'y' motion stage 32 and a linear 'x' motion stage 34, which operates at a right angle to the linear 'y' motion stage 32. The 'y' motion stage 32 moves normal to the plane of the drawing. The 'x' motion stage 34 moves horizontally. Linear motion stages 32 and 34 allow all possible locations on the wafer surface to be positioned at the measurement position 47 for the test sample 24. Also contained within the test chamber is a 'phi' (f) rotation stage 36 onto which the linear 'x' motion stage 32 and linear 'y' motion stage 34 are mounted. The phi rotation stage 36 allows for control of X-ray projection direction from the measuring head 40 onto the surface of the test sample 24. The phi rotation stage 36 is mounted so that its center of rotation is directly below the measurement position 47. By mounting the linear stages 32 and 34 on top of the phi rotation stage 36, the center of rotation of test sample 24 is always fixed at the center of the test chamber 22 footprint regardless of the 'x' and 'y' location and directly underneath the measurement position 47. It is important that the measurement position 47, as defined by where X-ray beam 46 impinges upon test sample 24, is aligned to be on the axis of the center of rotation of the phi rotation stage. The size of the test chamber 22 and the travel limits of the linear stages 32 and 34 are made large enough to enable any location on the test sample 24 to be positioned at the center measurement position. Movements of the beta goniometer 60, the vertical motion stage 64, the linear 'y' motion stage 32, the linear 'x' motion stage 34, and the phi rotation stage 36, are controlled by commercially available encoded stepper (or servo) drive motors in response to commands from the controller 37.

An incident X-ray beam 46 readily penetrates the X-ray window 45 and is diffracted from the test sample 24. The X-ray window 45 itself is attached to the thermal barrier top plate 38. Diffraction occurs in the crystalline grains near the surface of the test sample at particular angular orientations. Diffracted X-ray beams 49 and 51 pass back through the X-ray window 45 and impinge upon end surfaces of the fiber-optic detectors 48 and 50 respectively. During the X-ray diffraction method of stress analysis described in U.S. Pat. No. 4,686,631, the detectors are positioned on the detector mounting arc 52 at an appropriate 2θ angle for collecting a high back reflected diffraction peak of the test sample. The X-rays diffracting off the test sample surface actually form a conical shape about the incident X-ray beam 46. For test measurement purposes, only two short segments of the sides of the conical shaped diffracted rays are used. These two short segments are incident upon signal receiving end surfaces, 31 and 33, of the fiber-optic detectors 48 and 50, respectively.

The long dimension of the X-ray window 45 accommodates rotation of the X-ray source and the detectors through a wide range of $\Psi$ angles necessary for the $\sin^2\Psi$ stress measurement technique. The 'x' and 'y' linear motion stages enable measurement of stress at any location on the test sample. The phi rotation stage enables measurement of stress in any radial direction at any location on the test sample.

The X-ray window 45 is appropriately thin and of sufficiently low atomic number to let a large percentage of the X-ray beam pass through while providing a barrier to the movement of gases. The X-ray window must also be capable of withstanding elevated temperatures to near 500° C., which is the desired maximum temperature of the test sample. A preferred embodiment of the X-ray window 45 employs a beryllium foil that is between three and ten mils thick with a chemically inert protective coating on both sides. The chemically inert coating is less than ten microns thick and provides improved oxidation resistance at elevated temperatures. Such a coated beryllium X-ray window material can be obtained from Moxtek Inc. Most of the heat escaping from the heated zone above wafer 24 will pass through the X-ray window 45. For maximum thermal resistance, an optional second X-ray window of the same size can be placed on top of the first window but separated by a narrow space. This is similar in principle to double pane glass used to increase thermal resistance of architectural windows. It is advantageous to make the X-ray window area small. The size of the window is described in greater detail with regard to FIG. 2.

The measuring head 40 includes signal receiving surfaces, or detector faces, 31 and 33 with scintillation material coated on a thin plastic film that is affixed to the X-ray receiving ends of the fiber-optic bundles 48 and 50. The thin plastic film may be coated with aluminum. The scintillation material converts the received X-ray energy into visible light energy. Useful scintillation coatings include gadolinium oxy-sulfide doped with turbium, cesium iodide doped with sodium, and zinc sulfide doped with cadmium. The scintillation coating is deposited to a thickness in a range from 20 microns to 50 microns.

Since the diffracted X-ray energy has position associated variation of intensity, the resulting visible light also has position sensitive variations of intensity correlating with the variations of the X-rays.

There are two fiber-optic bundles 48 and 50, each bundle having a rectangular cross-section at both the signal receiving surfaces 31 and 33 and the detector ends 35. The fibers in each bundle are mapped at both ends to have the same array positions at each end. Each fiber transmits the received visible light impinging thereupon, e.g., at the end adjacent the signal receiving surface 31, to the detector end 35 in an array position, for the bundle 48, similar to its position at the end adjacent the receiving surface 31.

X-rays incident on the signal receiving surfaces 31 and 33 include background level intensity and diffraction peak level intensity. The conversion from X-rays to visible light retains the relative magnitudes of the different intensities. The fiber-optic bundles retain the positional variations of intensity while transmitting the visible light to the photo detector ends 35.

The detector ends 35 of the fiber-optic X-ray detectors 48 and 50 are connected to a fixed photo-sensor array 68 of a high performance charge couple device (CCD) and an image intensifier. Fiber-optic bundles can be fabricated to desired dimensions by Schott Fiber Optics. The size of the photo-sensor array is selected to match the size of the fiber-optics. The X-ray detectors 48 and 50 are sufficiently long and flexible so that the measuring head 40 can be rotated without adversely affecting the connection of detectors 48 and 50 to the photo-sensor array 68. A more complete description of a CCD in combination with fiber-optic bundles for use as X-ray detectors is presented in a patent application Ser. No. 08/823,971 filed Mar. 25, 1997 in the name of David S. Kurtz for "TWO-DIMENSIONAL PHOTO-SENSOR FIBER-OPTIC STRESS ANALYSIS SYSTEM". The measuring head 40, the X-ray source and housing 56, the beta goniometer 60, the z-axis stage 64, and the photo-sensor array 68 are mounted to a common support 66. Operation of the CCD is directed by a CCD controller 69. The operations of the CCD controller 69, an X-ray source controller 57, the multiple motion stage controller 37, and the test sample heater controller 25, are centrally controlled from a single computer 70 which coordinates all of the separate functions. As a system the entire test apparatus 20 provides complete wafer mapping, complete directional stress measurement, and complete thermal cycling.

Figure 2:
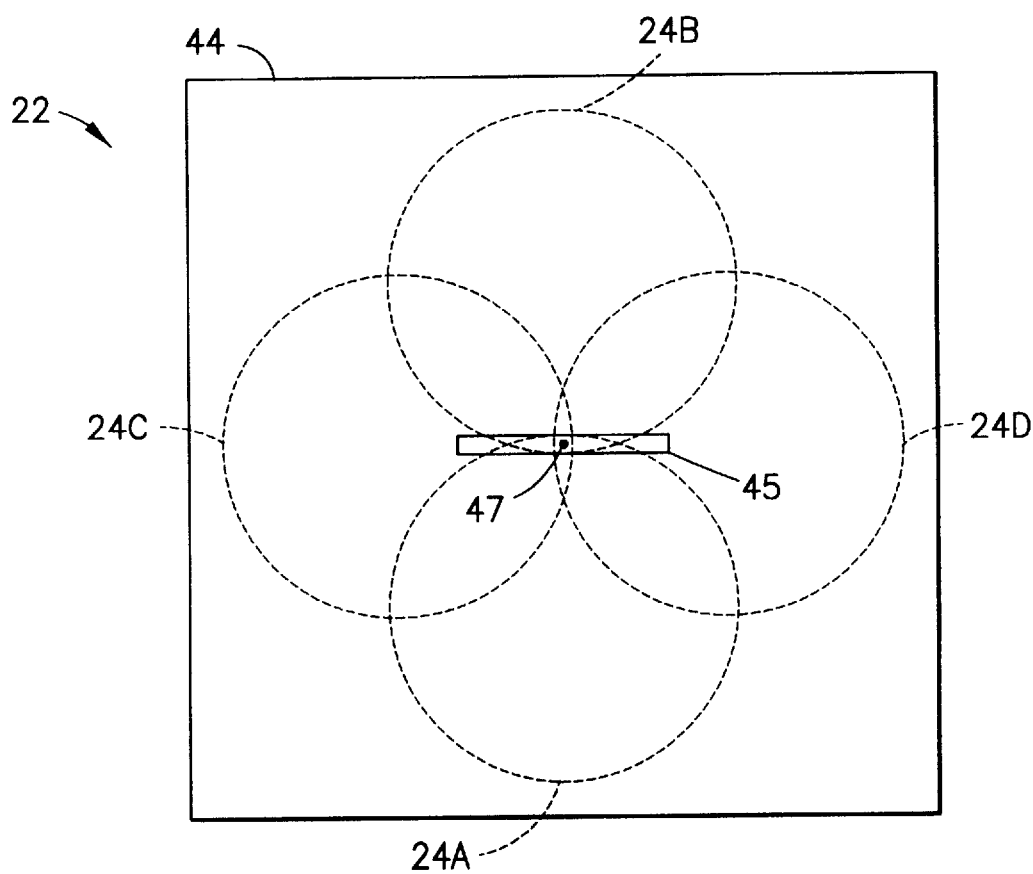
FIG. 2 is a schematic diagram of the top view of a thermal barrier plate between a measuring head and a wafer; the diagram illustrating X-ray window dimensions and possible wafer positions.

Referring now to FIG. 2, a top view looking down on the test chamber 22 is shown depicting the size of the test chamber 22 and of the X-ray window 45. The bottom plate 44 is shown with a foot print that accommodates all possible test locations on test sample 24, shown in four dotted positions. As an example a circular wafer is shown as the test sample 24. The wafer is in its furthest forward location at dotted position 24A, its furthest aft location at dotted position 24B, its furthest left location at dotted position 24C, and its furthest right location at dotted position 24D. An eight inch diameter wafer would require a test chamber 22 having a foot print at least sixteen inches across both ways plus some small overage factor accounting for the size of the motion stages and heater. Other foot print shapes, such as a circular shape, also can be used.

Rotation of the measuring head 40 in FIG. 1 along the beta arc 59 in a side-to-side movement determines in part a desirable length of the X-ray window 45. The X-ray beam diffracting off measurement position 47 should reach both detectors while the incident beam is at a large beta angle. Based on a beta angle of 30° and a usable 2θ angle of 120°, the length of the X-ray window 45 falls in a range from approximately fourteen centimeters to twenty-two centimeters.

The width of the X-ray window 45 is as wide as the X-ray beam itself, since the measuring head 40 is never moved from front to aft. Keeping the width of the X-ray window 45 small greatly reduces heat transfer from the test chamber 22 to the measuring head 40 since the remainder of the top thermal barrier plate 38 is made of a high thermal resistance material. A narrow X-ray window 45 will also be less costly and less susceptible to accidental physical damage. The size of the X-ray beam can be controlled by a collimating aperture housed within the shutter assembly 54. A typical X-ray beam size may be one millimeter in diameter, but can range in size from ten microns (with a micro-diffraction capillary) to five millimeters in diameter. An X-ray window 45 width of four to eight millimeters can be used and still allow for slight alignment error of the X-ray beam 46 diameter.

Figure 3:
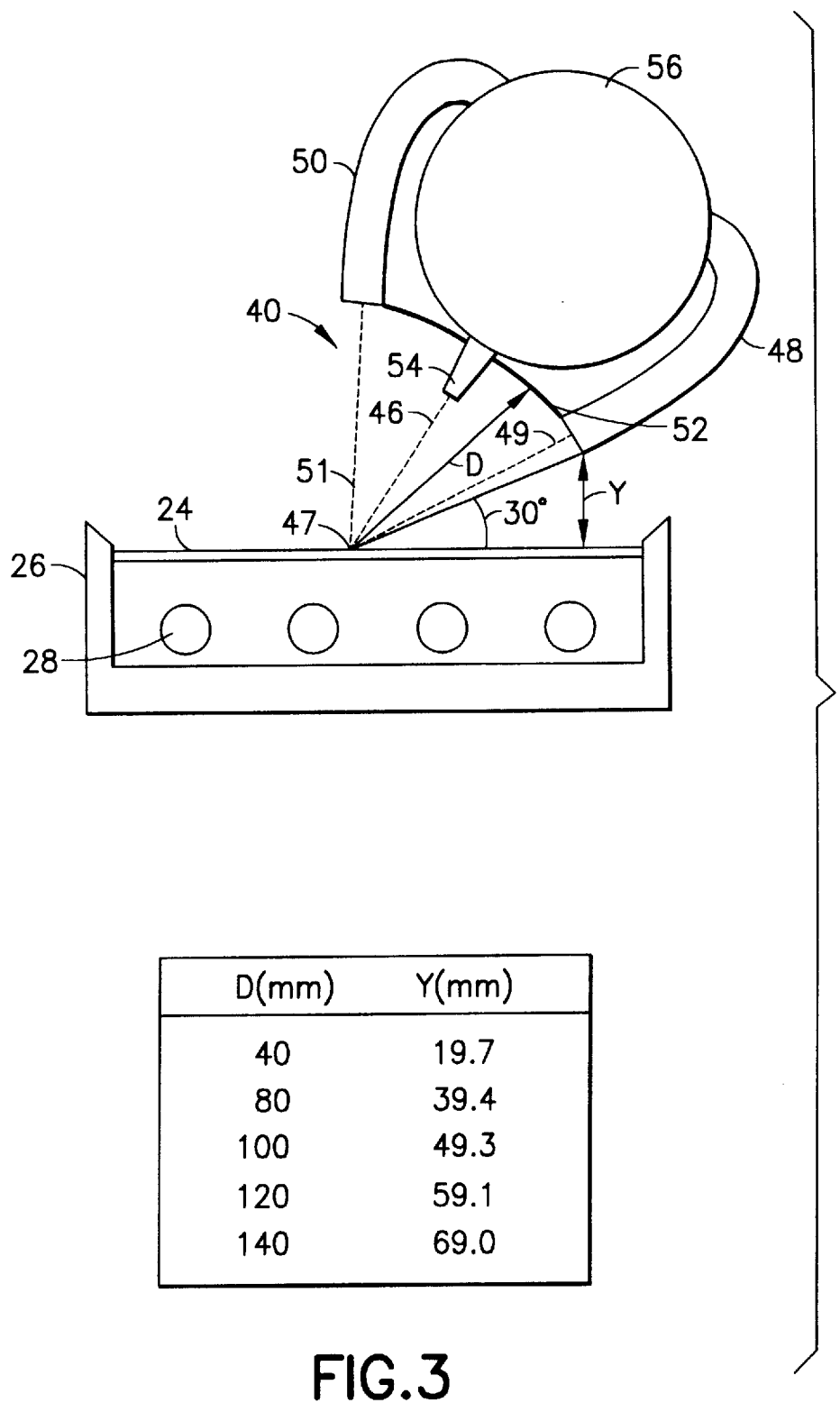
FIG. 3 is a schematic diagram showing the proximity of the measuring head to the sample being tested.

Referring now to FIG. 3, D represents the working distance, which is defined as the distance from the measurement position 47 to the detector mounting arc 52. When the measuring head is rotated clockwise on the beta goniometer 60 from FIG. 1, the vertical separation distance Y from the lowest part of the fiber-optic detector 48 to the test sample 24 surface becomes very small. A typical lower angular limit between diffracted beam 49 and the test sample 24 surface is 30°. The vertical separation distance Y can be increased by increasing the working distance D. The table in FIG. 3 shows that for a working distance D of forty millimeters, as conventionally practiced in U.S. Pat. No. 4,686,631, the vertical separation distance Y is only 19.7 millimeters. Maintaining a temperature of 500° C. uniformly across test sample 24 while keeping detector 48 near room temperature would be very difficult with such a short separation distance. A similar problem would exist with detector 50 when the measuring head 40 is rotated counterclockwise on beta goniometer 60.

At a working distance D of one hundred millimeters, the vertical separation distance Y is increased to 49.3 millimeters, a distance that is sufficient to accommodate the top thermal barrier plate 38.

Figure 4:
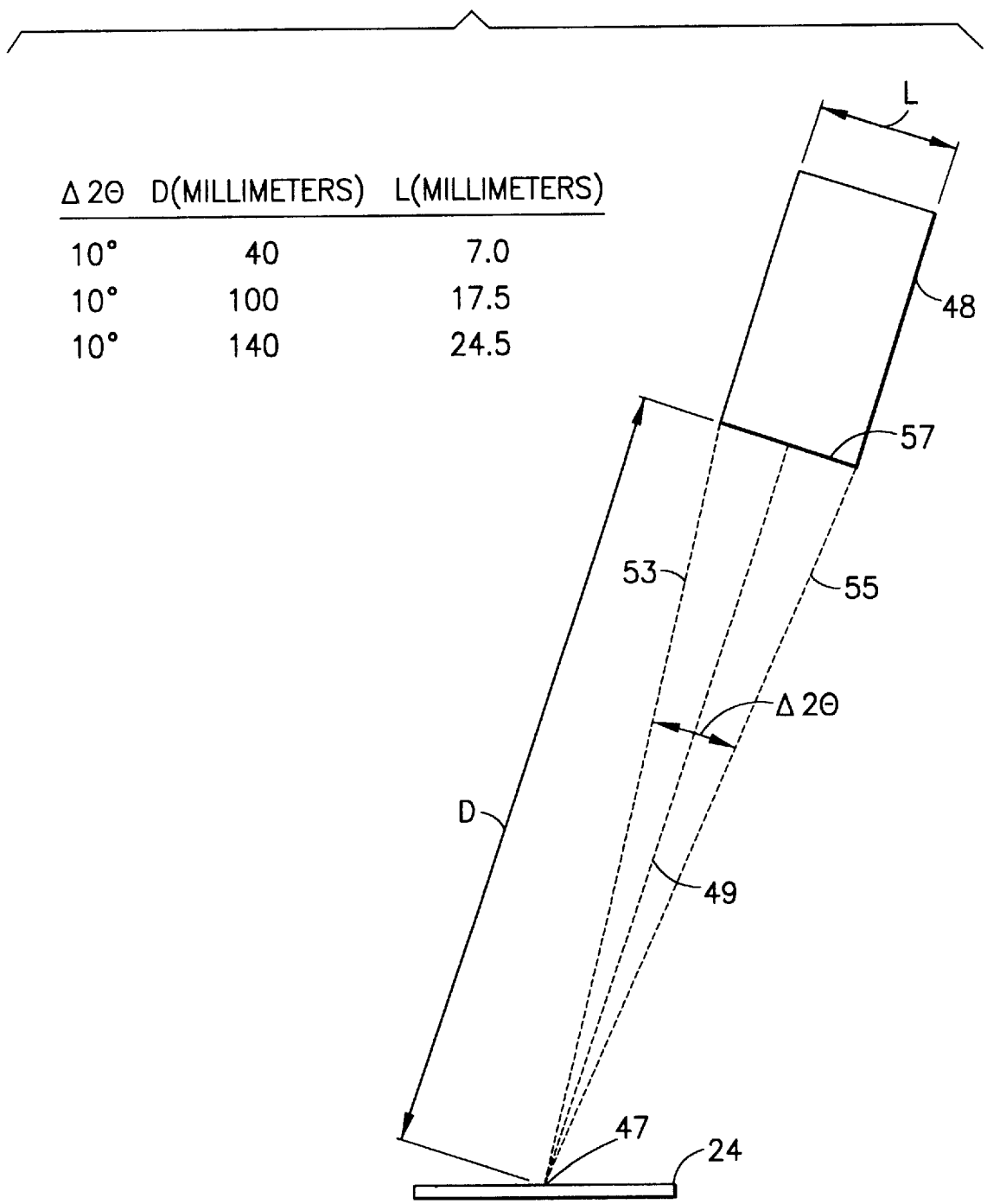
FIG. 4 shows the geometrical relationship between the working distance D and required detector size L.

Referring now to FIG. 4, the fiber-optic detector 48 will capture X-rays over an angular range. The center of the diffracted X-ray beam 49 will actually extend from an upper angular limit 53 to a lower angular limit 55. The angular range of X-rays captured by detector 48 is defined by the length L of the detector surface 57, and the working distance D, and is referred to as $\Delta 2\theta$ in FIG. 4. For most stress measurements, the angular range $\Delta 2\theta$ of detector 48 is about 10°. Thus the surface 57 of detector 48 should be long enough to cover an angular range $\Delta 2\theta$ of 10°. Approximately 10° captures the diffraction peak plus a sufficient amount of background on either side. When the working distance D is increased, the length L of the detector surface 57 of fiber-optic detector 48 should also be increased. At a working distance D of forty millimeters, the detector surface 57 has a length of seven millimeters. At a working distance D of one hundred millimeters, the detector surface 57 has a length of 17.5 millimeters; and at a D of one hundred forty millimeters, the detector surface 57 has a length of 24.5 millimeters.

The angular range $\Delta 2\theta$ can be widened and extended to longer working distances D, by the optional use of fiber-optic tapers or fiber-optic reorganizers. A suitable fiber-optic reorganizer is described in detail in a U.S. patent application, Ser. No. 08/590,956, filed Jan. 24, 1996 in the names of D. S. Kurtz and C. O. Ruud. Such patent application is incorporated herein by reference thereto. A working distance D in the range from one hundred millimeters to two hundred millimeters is expected to be effective for standard semiconductor wafers having diameters in a range between two hundred and three hundred millimeters.

Figure 5:
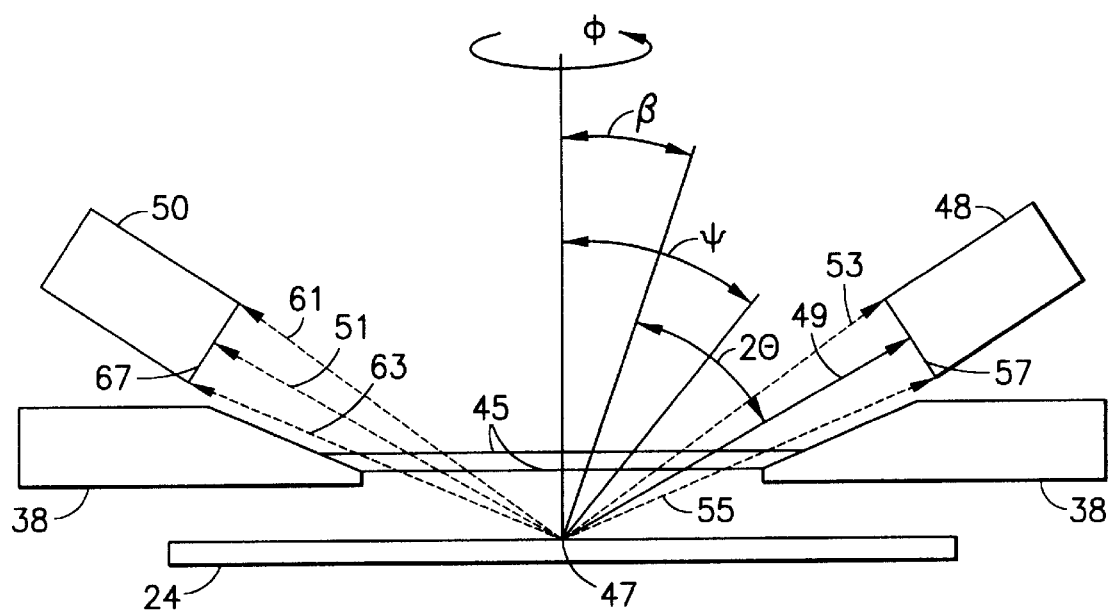
FIG. 5 shows a side view of the arrangement of the test sample, the detectors, the thermal barrier face, and the X-ray window.

FIG. 5 presents a close up detail of one preferred geometrical embodiment of the thermal barrier plate 38 and X-ray window 45 in proximity to the test sample 24 and fiber-optic detectors 48 and 50. An example of a two hundred millimeter silicon wafer is considered. The working distance D, which is equivalent to the length of diffracted X-ray beams 49 and 51 is set at one hundred millimeters. The active length of each detector face 57 and 67 is twenty-four millimeters providing a total angular range $\Delta 2\theta$ of 13.7°. The lower angular limit of the diffracted X-ray beams 49 and 51 is set at 30° from the test sample plane. This lower limit would correspond to a maximum beta angle of 30° coupled to a $2\theta$ angle of 120°. Thus FIG. 5 represents the lowest possible elevations of fiber-optic detectors 48 and 50 with respect to the test sample 24. The lowest angle of diffracted X-rays that each detector must be able to collect is represented, respectively, by diffracted X-ray lines 55 and 63. The angles created by these X-rays are actually slightly less than the 30° from the surface of the test sample 24. Thermal barrier plate 38 is fabricated to a maximum thickness of twenty millimeters, but tapers down to allow passage of the X-ray beam. A fourteen millimeter gap exists between the top of the test wafer 24 and the bottom of the thermal barrier plate 38. Two X-ray windows 45 are used. The upper one has a length of six centimeters and a width of four millimeters. The lower X-ray window 45 has a length of five centimeters and a width of four millimeters. In this configuration a high degree of thermal protection is provided to the detectors 48 and 50 while they are at their lowest elevation during any measurement sequence. At other times during the measurement sequence, they will be at higher elevations and less susceptible to heat damage.

As part of this embodiment of the present invention, one can employ a rectangular front illuminated scientific grade charge coupled device, as a photo-sensor array. The long dimension of the CCD is 0.027 millimeters per pixel by 1024 pixels, or 27.6 millimeters. The width is 0.027 millimeters per pixel by 256 pixels, or 6.9 millimeters. This CCD can be mated to a twenty-five millimeter diameter image intensifier such that 24.6 millimeters by 6.9 millimeters of the CCD cross-section will be fully usable. The image intensifier is a variable gain, gated device. Two bundles of optical fibers, each with a cross section of 24.6 millimeters by 3.3 millimeters, are mated to the CCD. A 0.15 millimeter thick light tight separating film is interposed between the two bundles of optical fibers. Details of the procedure for creating an X-ray detector from a CCD and fiber-optic bundles can be found in the previously mentioned patent application Ser. No. 08/823,971 filed Mar. 25, 1997 in the name of David S. Kurtz for "TWO-DIMENSIONAL PHOTO-SENSOR FIBER-OPTIC STRESS ANALYSIS SYSTEM". A multi-pin phasing option; thermoelectric heating; water cooling; nitrogen purging; and a slow scan readout are provided. Information in the CCD can be read out over time periods that are controlled by the user.

For the foregoing exemplary configuration, 24.6 millimeters of active detector length are available in the $2\theta$ direction thus satisfying the design length of detector faces 31 and 33 in FIG. 5. Approximately 3.3 millimeters of detector width are available perpendicular to the $2\theta$ direction. The working distance of the CCD array is very large for the angular range. The increase in working distance is critical for in-situ thermal stress measurements since the test sample 24 is kept at a uniform elevated temperature, while the measuring head 40 is held close to room temperature.

During a test for stress in a thin film, the X-ray beam is held on for a duration that is sufficiently long to enable the CCD detector 68 of FIG. 1 to collect a sufficient peak signal above the background signal for subsequent data processing. Quickness of data collection is important if the measurement is to keep up with the heating and cooling rate of a typical semiconductor thermal cycle process. Stress can be determined at different locations on the test sample 24 surface.

Both single exposure test (SET) stress measurements where the measuring head 40 is fixed at only one position on the beta goniometer 60 and multiple exposure test (MET) stress measurements where the measuring head 40 acquires data at several different positions on the beta goniometer 60 can be made. The radial projected direction of the incident x-ray beam as determined by the beta arc 59 for any point on the test sample can be controlled. It is desirable to be able to carry out all of these operations without extensive reconfiguration of the apparatus.

The thermal X-ray stress apparatus 20 of FIG. 1 has special features that allow it to perform all of the desired functions described in the previous paragraph. The full detector including the fiber-optic bundles 48 and 50 and the 2-D photo-sensor array 68 is very sensitive and correspondingly fast compared to a previous fiber-optic based detector described in U.S. Pat. No. 4,686,631, U.S. Pat. No. 5,148,458, and U.S. Pat. No. 5,414,747. The aforementioned U.S. patents are incorporated herein by reference thereto. A complete description of a data binning arrangement is presented in the previously mentioned and concurrently filed patent application, Ser. No. 08/823,971 filed Mar. 25, 1997 in the name of David S. Kurtz for "TWO-DIMENSIONAL PHOTO-SENSOR FIBER-OPTIC STRESS ANALYSIS SYSTEM". The apparatus can be fabricated with a longer face dimension L allowing for a larger minimum vertical separation distance Y, which in turn enables the incorporation of a thermal barrier plate 38 and enhanced temperature uniformity and control of the test sample 24 and measuring head 40.

The combination of the test chamber 22 including x motion, y motion, phi motion, and heating control and the measuring head 40 including 'beta' motion and 'z' motion control, provides all of the desired stress measurement motions to be performed during the thermal cycling process without other modification of the apparatus. It enables the use of a thermal barrier plate 38 using only a single narrow X-ray window which minimizes heat conduction to the measuring head 40.

The foregoing describes an X-ray stress measurement test apparatus and method for measuring stress in a test sample. The described apparatus and test method together with other apparatus and test methods, made obvious in view thereof, are considered to be within the scope of the appended claims.

What is claimed is:

1. An x-ray diffraction apparatus for rapid in-situ x-ray stress measurement of a substantially planar wafer sample having a top surface on which a beam of x-radiation is impinged during thermal cycling thereof, said apparatus comprising:

a thermal cycling chamber defining an enclosed interior volume and bounded at an upper end of the thermal cycling chamber by a thermal barrier plate confining elevated temperature conditions to the interior volume, said thermal barrier plate having a slit opening therein with a slit opening width generally corresponding to beam width of said beam of x-radiation, and with a slit opening length greater than the slit opening width;

an x-radiation-transmissive window mounted in said slit opening;

means for mounting the wafer sample in the interior volume of the thermal cycling chamber beneath said window;

means arranged for translating the wafer sample within the interior volume of the thermal cycling chamber and beneath said window, so that any selected point on the top surface of the wafer sample is positionable to receive x-radiation transmitted through said window;

means for cyclically heating and cooling the wafer sample in said thermal cycling chamber;

a measuring head and detector assembly overlying the thermal cycling chamber, said measuring head and detector assembly including:

a beta goniometer defining an arcuate travel path;

an x-radiation source mounted on said goniometer so as to be arcuately moveable thereon along the arcuate travel path, whereby the x-radiation source is selectively positionable on the goniometer to direct an x-ray beam at a selected x-ray β angle through the window onto a measurement position on the wafer sample top surface beneath said window, so that x-radiation is back-reflected from said wafer sample top surface through said window;

a detector mounting arc defining an arc radius of curvature;

an x-radiation detector mounted on said detector mounting arc to detect back-reflected x-radiation from the wafer sample top surface; and means for vertically elevationally adjusting the measuring head and detector assembly, to obtain a working distance between said x-radiation source and said measurement position that is equal to the arc radius of curvature of the detector mounting arc for said x-ray stress measurement.

2. An x-ray diffraction apparatus according to claim 1, wherein two x-radiation detectors are mounted on said detector mounting arc in spaced relationship to one another.

3. An x-ray diffraction apparatus according to claim 2, wherein each of said x-radiation detectors comprises a fiber optic bundle presenting an input face to said back-reflected x-radiation, said input face including a scintillation material coating for conversion of said back-reflected x-radiation to light, and said fiber optic bundle terminating in an opposite output face.

4. An x-ray diffraction apparatus according to claim 3, wherein the output face of the fiber optic bundle is mated to a correspondingly sized photosensor array of a charge coupled device and image intensifier assembly.

5. An x-ray diffraction apparatus according to claim 1, wherein the thermal barrier plate and thermal cycling chamber are insulatively effective to maintain the measuring head and detector assembly at room temperature level when said means for cyclically heating and cooling the wafer sample are operated to provide a wafer sample temperature range of from 0° C. to 500° C.

6. An x-ray diffraction apparatus according to claim 1, further comprising a skirt member surrounding the wafer sample and extending upwardly therefrom to an upper end terminating in proximity to the thermal barrier plate, to define a zone for confined heating of the wafer sample during said heating of the wafer sample in said thermal cycling chamber.

7. An x-ray diffraction apparatus according to claim 1, further comprising means for flowing a purge gas into the thermal cycling chamber, and for purging the purge gas from the thermal cycling chamber.

8. An x-ray diffraction apparatus according to claim 1, further comprising means for establishing vacuum in the thermal cycling chamber.

9. An x-ray diffraction apparatus according to claim 1, wherein said means for cyclically heating the wafer sample in said thermal cycling chamber comprise resistive heating elements.

10. An x-ray diffraction apparatus according to claim 1, wherein said means for cyclically heating the wafer sample in said thermal cycling chamber comprise a thermal chuck.

11. An x-ray diffraction apparatus according to claim 1, wherein said means for cyclically heating and cooling the wafer sample in said thermal cycling chamber comprise a programmable temperature controller.

12. An x-ray diffraction apparatus according to claim 1, wherein said slit opening width is from about 4 to about 8 millimeters.

13. An x-ray diffraction apparatus according to claim 1, wherein said means for vertically elevationally adjusting the measuring head and detector assembly provide a working distance in the range of from about 40 to about 200 millimeters.

14. An x-ray diffraction apparatus according to claim 1, wherein:

the slit opening has a length-to-width ratio of at least fifteen.

15. An x-ray diffraction apparatus according to claim 1, wherein:

the x-radiation-transmissive window is made of beryllium with a chemically inert coating on each side.

16. An x-ray diffraction apparatus according to claim 3, wherein:

the scintillation material coating comprises gadolinium oxy-sulfide doped with terbium and deposited to a thickness in the range from 20 microns to 50 microns on a plastic film coated with aluminum.

* * * * *

UNITED STATES PATENT AND TRADEMARK OFFICE
CERTIFICATE OF CORRECTION

PATENT : 5,848,122
DATED : December 8, 1998
INVENTOR(S) : David S. Kurtz

It is certified that error appears in the above-identified patent and that said Letters Patent is hereby corrected as shown below:

In column 1, between lines 5 and 6, insert the following:

--The invention was made with support of the U.S. Government under contract F30602-96-C-0107 awarded by the Department of the Air Force, Wright Patterson Air Force Base. The Government has certain rights in this invention.--.

Signed and Sealed this

Eighteenth Day of May, 1999

Attest:

Q. TODD DICKINSON

*Attesting Officer*     *Acting Commissioner of Patents and Trademarks*